(12) United States Patent
Shim et al.

(10) Patent No.: US 10,335,341 B2
(45) Date of Patent: Jul. 2, 2019

(54) WALKING ASSISTANCE METHOD AND APPARATUS

(71) Applicant: Samsung Electronics Co., Ltd., Suwon-si, Gyeonggi-do (KR)

(72) Inventors: Youngbo Shim, Seoul (KR); Jongwon Lee, Gyeonggi-do (KR); Youngjin Park, Seoul (KR); Sunghwan Ahn, Seoul (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 680 days.

(21) Appl. No.: 14/879,481

(22) Filed: Oct. 9, 2015

(65) Prior Publication Data

US 2016/0206499 A1 Jul. 21, 2016

(30) Foreign Application Priority Data

Jan. 21, 2015 (KR) .......................... 10-2015-0009954

(51) Int. Cl.
*A61H 3/00* (2006.01)
*A61F 2/70* (2006.01)
*G09B 19/00* (2006.01)
*A61B 5/103* (2006.01)
*A61B 5/11* (2006.01)
*A61B 5/00* (2006.01)

(52) U.S. Cl.
CPC ............. *A61H 3/00* (2013.01); *A61B 5/1038* (2013.01); *A61B 5/112* (2013.01); *A61F 2/70* (2013.01); *G09B 19/003* (2013.01); *A61B 5/6807* (2013.01); *A61B 2562/0247* (2013.01)

(58) Field of Classification Search
CPC ......... A61H 3/00; A61B 5/1038; A61B 5/112; A61F 2/70; G09B 19/003
USPC ........................................................ 434/247
See application file for complete search history.

(56) References Cited

U.S. PATENT DOCUMENTS

| 8,308,665 | B2 | 11/2012 | Harry et al. |
| 8,428,737 | B2 | 4/2013 | Endo et al. |
| 8,773,148 | B2 | 7/2014 | Sankai et al. |
| 2007/0203435 | A1 | 8/2007 | Novak |
| 2009/0240171 | A1* | 9/2009 | Morris Bamberg ........................ A61B 5/1038 600/595 |

(Continued)

FOREIGN PATENT DOCUMENTS

| JP | H08511975 A | 12/1996 |
| JP | 2004141275 A | 5/2004 |

(Continued)

OTHER PUBLICATIONS

Extended European Search Report issued by the EPO dated Jun. 28, 2016 for corresponding EP Patent Application No. 15198152.9.

(Continued)

*Primary Examiner* — Robert P Bullington
(74) *Attorney, Agent, or Firm* — Harness, Dickey & Pierce, P.L.C.

(57) ABSTRACT

A walking assistance method and apparatus, in detail, a control device that may estimate a gait motion of a user based on pressure data indicating information on a pressure applied to a sole of the user, and provide a feedback corresponding to the gait motion to the user by controlling a vibrator to apply a vibration to the sole of the user, is provided.

23 Claims, 16 Drawing Sheets

(56) References Cited

U.S. PATENT DOCUMENTS

| | | | |
|---|---|---|---|
| 2012/0154153 A1* | 6/2012 | Agrawal | A61B 5/0051 340/573.1 |
| 2014/0142475 A1 | 5/2014 | Goldfarb et al. | |
| 2016/0045386 A1* | 2/2016 | Sandler | A61B 5/7415 623/24 |

FOREIGN PATENT DOCUMENTS

| | | |
|---|---|---|
| JP | 2010273748 A | 12/2010 |
| JP | 2013138793 A | 7/2013 |
| KR | 100615446 B1 | 8/2006 |
| KR | 20080099752 A | 11/2008 |
| KR | 20100121309 A | 11/2010 |
| KR | 101134213 B1 | 4/2012 |
| KR | 20130010609 A | 1/2013 |
| KR | 101302364 B1 | 9/2013 |

OTHER PUBLICATIONS

Peter Novak et al. "Effect of step-synchronized vibration stimulation of soles on gait in Parkinson's disease: a pilot study". Journal of NeuroEngineering and Rehabilitation.May 4, 2006. pp. 1-7.
Andrew M. Galica et al. "Subsensory Vibrations to the Feet Reduce Gait Variability in Elderly Fallers". NIH Public Access: Author Manuscript. Oct. 2009. p. 1-13.

* cited by examiner

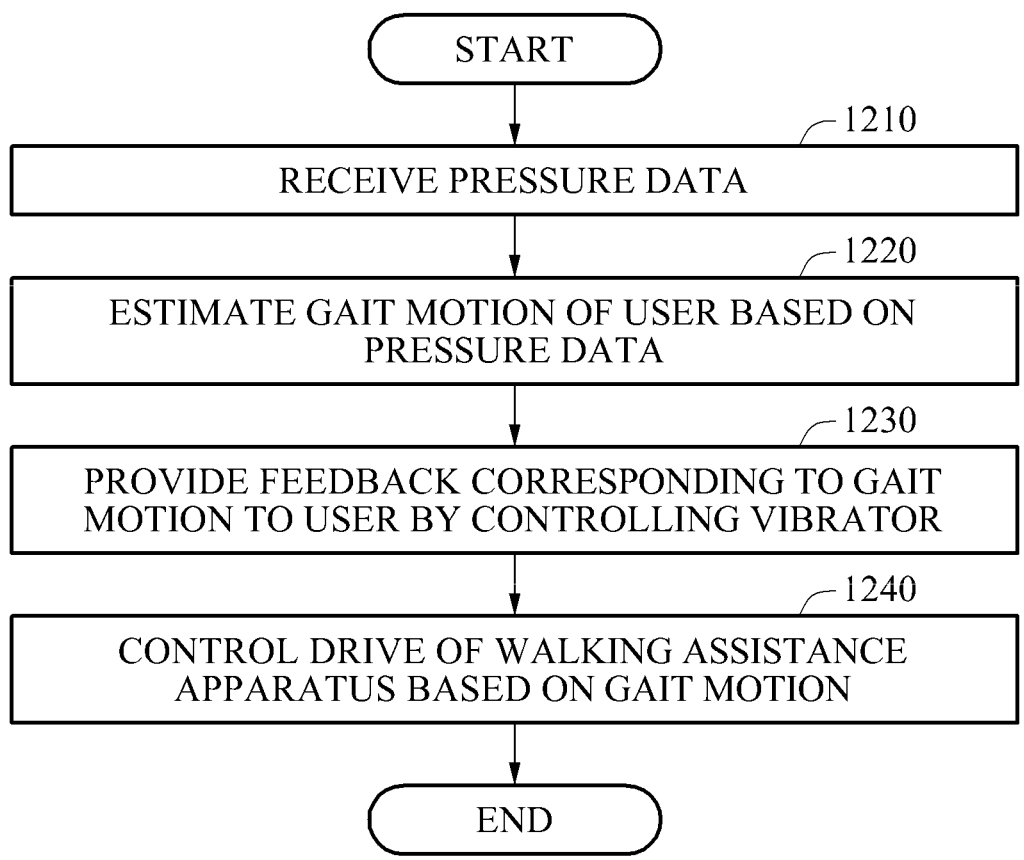

WALKING ASSISTANCE METHOD AND APPARATUS

CROSS-REFERENCE TO RELATED APPLICATION

This application claims the priority benefit of Korean Patent Application No. 10-2015-0009954, filed on Jan. 21, 2015, in the Korean Intellectual Property Office, the entire contents of which are incorporated herein by reference in its entirety.

BACKGROUND

1. Field

Example embodiments relate to a walking assistance method and/or apparatus.

2. Description of the Related Art

With the onset of rapidly aging societies, many people are experiencing inconvenience and/or pain from joint problems. Thus, a motion assistance apparatus that enables the elderly and/or patients having joint problems to walk with less effort may be desirable. Furthermore, motion assistance apparatuses for intensifying muscular strength of human bodies may be useful for military purposes.

SUMMARY

Some example embodiments relate to a control device.

In some example embodiments, the control device may include a gait data receiver configured to receive pressure data indicating information on a pressure applied to a sole of a user, a gait motion estimator configured to estimate a gait motion of the user based on the pressure data, and a feedback provider configured to provide a feedback corresponding to the gait motion to the user by controlling a vibrator to apply a vibration to the sole of the user.

The gait data receiver may be configured to receive the pressure data from a pressure sensor attached to a surface in contact with the sole of the user.

The gait data receiver may be configured to receive the pressure data from the pressure sensor using a communication interface.

At least two pressure sensors may be provided, and the at least two pressure sensors may be configured to generate the pressure data by sensing a pressure applied to a front portion of the sole and a pressure applied to a rear portion of the sole.

The gait motion estimator may be configured to estimate a gait motion of touching the ground with the front portion of the sole and a gait motion of touching the ground with the rear portion of the sole based on the pressure data.

The feedback provider may be configured to operate the vibrator based on the estimation of the gait motion of touching the ground with the front portion of the sole and the gait motion of touching the ground with the rear portion of the sole.

The feedback provider may be configured to adjust a vibration intensity of the vibrator based on a shift in a center of pressure (COP) of the sole with respect to the gait motion.

The gait data receiver may be configured to receive hip joint angle data indicating information on a hip joint angle of the user.

The feedback provider may be configured to estimate the COP based on the pressure data and the hip joint angle data.

The feedback provider may be configured to estimate the COP based on information on changes in pressures applied to the front portion and the rear portion of the sole included in the pressure data.

The gait motion estimator may be configured to model gait motions of the user as a plurality of gait states, and estimate a gait state corresponding to a current gait motion of the user, among the modeled plurality of gait states, based on the pressure data and the hip joint angle data, and the feedback provider may be configured to control the vibrator based on the estimated gait state.

The control device may further include a drive controller configured to control a drive of a walking assistance apparatus based on the gait motion.

The drive controller may be configured to generate a control signal to drive the walking assistance apparatus based on the estimation of the gait motion of touching the ground with the front portion of the sole and the gait motion of touching the ground with the rear portion of the sole.

The at least two pressure sensors may be configured to generate the pressure data by sensing a pressure applied to a left portion of the sole and a pressure applied to a right portion of the sole, and the gait motion estimator may be configured to determine whether the gait motion of the user is balanced based on the pressure data.

The feedback provider may be configured to operate the vibrator when the gait motion estimator determines the gait motion of the user is unbalanced.

The drive controller may be configured to control the drive of the walking assistance apparatus for the gait motion of the user to be balanced when the gait motion estimator determines the gait motion of the user is unbalanced.

Other example embodiments relate to a walking assistance apparatus.

In some example embodiments, the walking assistance apparatus may include an additional device including a pressure sensor configured to generate pressure data indicating information on a pressure applied to a sole of a user, a hip joint angle sensor configured to generate hip joint angle data indicating information on a hip joint angle of the user, a vibrator configured to apply a vibration to the sole of the user and, a processor configured to receive the pressure data and the hip joint angle data, estimate a gait motion of the user based on the pressure data and the hip joint angle data, and provide a feedback corresponding to the gait motion to the user by controlling the vibrator.

At least two pressure sensors may be provided, and the at least two pressure sensors may be configured to generate the pressure data by sensing a pressure applied to a front portion of the sole and a pressure applied to a rear portion of the sole.

The at least two pressure sensors may be configured to generate the pressure data by sensing a pressure applied to a left portion of the sole and a pressure applied to a right portion of the sole, and the processor may be configured to determine whether the gait motion of the user is balanced based on the pressure data, and operate the vibrator when the gait motion of the user is determined to be unbalanced.

Other example embodiments relate to a control method.

In some example embodiments, the control method may include receiving pressure data indicating information on a pressure applied to a sole of a user, estimating a gait motion of the user based on the pressure data, and providing a feedback corresponding to the gait motion to the user by controlling a vibrator to apply a vibration to the sole of the user.

The control method may further include controlling a drive of a walking assistance apparatus based on the gait motion.

Other example embodiments relate to a control method.

In some example embodiments, the control method may include generating pressure data by sensing a pressure applied to a sole of a user, transmitting the pressure data to a walking assistance apparatus, receiving a vibrator control signal from the walking assistance apparatus, the vibrator control signal corresponding to a feedback generated by the walking assistance apparatus based on the pressure data, and controlling a vibrator based on the vibrator control signal.

The controlling may include operating the vibrator for a time period during which a gait motion of touching the ground with the sole of the user is performed.

The controlling may include adjusting a vibration intensity of the vibrator based on a shift in a COP of the sole.

Other example embodiments relate to a control device.

In some example embodiments, the control device may include a pressure sensor configured to sense a pressure applied to a sole of a user, a processor configured to generate pressure data based on the sensed pressure, a communication interface configured to transmit the pressure data to a walking assistance apparatus, and receive a vibrator control signal from the walking assistance apparatus, the vibrator control signal corresponding to a feedback generated by the walking assistance apparatus based on the pressure data, and a vibrator configured to apply a vibration based on the vibrator control signal. The processor may be configured to control the vibrator based on the vibrator control signal received by the communication interface.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 12 illustrates a control method according to example embodiments.

DETAILED DESCRIPTION

Figure 1A:
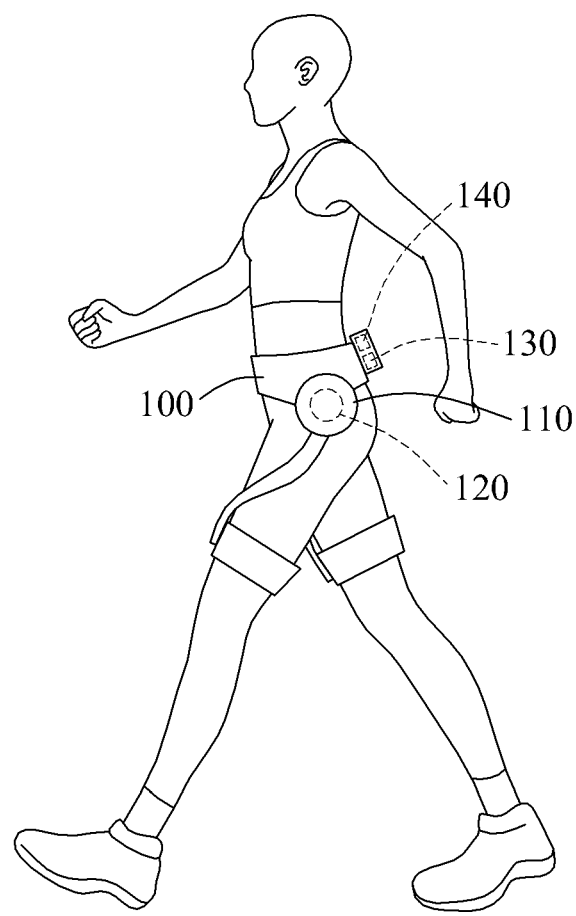
FIGS. 1A and 1B illustrate a walking assistance apparatus according to example embodiments.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description does not help in understanding the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 1B:
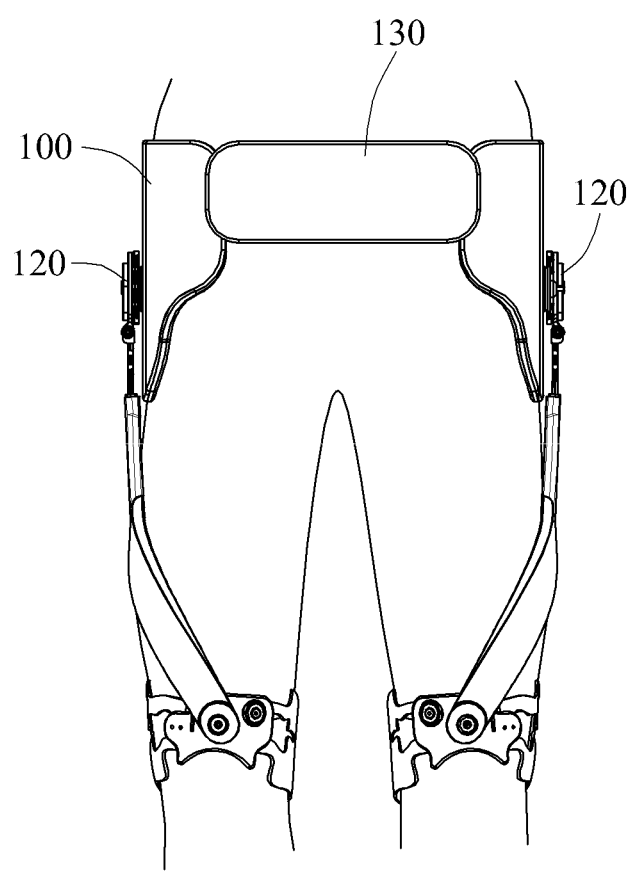

FIGS. 1A and 1B illustrate a walking assistance apparatus according to example embodiments.

Referring to FIGS. 1A and 1B, a walking assistance apparatus 100 may be attached to a user to assist walking of the user. The walking assistance apparatus 100 may include a driver 110, a sensor portion 120, an inertial measurement unit (IMU) sensor 130, and a controller 140.

Although FIGS. 1A and 1B illustrate a hip-type walking assistance apparatus, example embodiments are not limited thereto. For example, example embodiments may be applicable to a walking assistance apparatus that supports an entire pelvic limb, and a walking assistance apparatus that supports a portion of a pelvic limb. The walking assistance apparatus that supports a portion of a pelvic limb may include a walking assistance apparatus that supports down to a knee, and a walking assistance apparatus that supports down to an ankle. Example embodiments may also be applicable to a walking assistance apparatus that supports the entire body.

The driver 110 may be disposed on, for example, each of a right hip portion and a left hip portion of the user to drive both hip joints of the user. However, example embodiments are not limited thereto. For example, the driver 110 may be disposed on only one hip joint of the user.

The sensor portion 120 may each measure the hip joint angle information of the user while the user is walking. The hip joint angle information may include angle of the hip joint, a difference between the angles of both hip joints, and/or the motion direction of the hip joints. The sensor portion 120 may be disposed in the driver 110.

In an example, the sensor portion 120 may include a potentiometer. The potentiometer may sense R-axis and L-axis joint angles and/or R-axis and L-axis joint angular velocities with respect to a gait motion of the user.

The IMU sensor 130 may measure acceleration information and posture information while the user is walking. For example, the IMU sensor 130 may sense X-axis, Y-axis, and Z-axis accelerations and/or X-axis, Y-axis, and Z-axis angular velocities with respect to a gait motion of the user. The walking assistance apparatus 100 may detect a landing point of a foot of the user in time based on the acceleration information measured by the IMU sensor 130.

Further, the walking assistance apparatus 100 may include, in addition to the sensor portion 120 and the IMU sensor 130, another sensor that may sense a change in a biosignal or a quantity of motion of the user with respect to a gait motion. The other sensor may include, for example, an electromyography (EMG) sensor.

The controller 140 may control the driver 110 to output an assistance force or an assistance torque to assist walking of the user. For example, in the hip-type walking assistance apparatus 100, two drivers 110 may be provided and the controller 140 may output a control signal to the drivers 110 to output assistance forces corresponding to a gait motion. The drivers 110 may output assistance forces based on the control signal output from the controller 140. The assistance forces may be set by an external device, or set by the controller 140.

The controller 140 may include a memory and a processor (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processor into a special purpose computer to perform the operations illustrated in one or more of FIGS. 11 and 12, such that the processor is configured to receive pressure data from the pressure sensors 231, 232 (FIG. 2B), estimate the gait motion of the user based on the pressure data, and control the vibrators 233, 234 (FIG. 2B) based on the gait motion. Therefore, the walking assistance apparatus 100 may provide tactical feedback to a portion of the sole of the user touching the ground such that the user experiences sensations normally felt on the sole as he/she walks and/or that it informs the user that the gait motion is unbalanced. Further, the processor may be configured to control the driver 110 based on the gait motion. Therefore, the walking assistance apparatus 100 may output an assistance force that re-balances pressures applied to the left portion and the right portion of the sole of the user.

Figure 9:
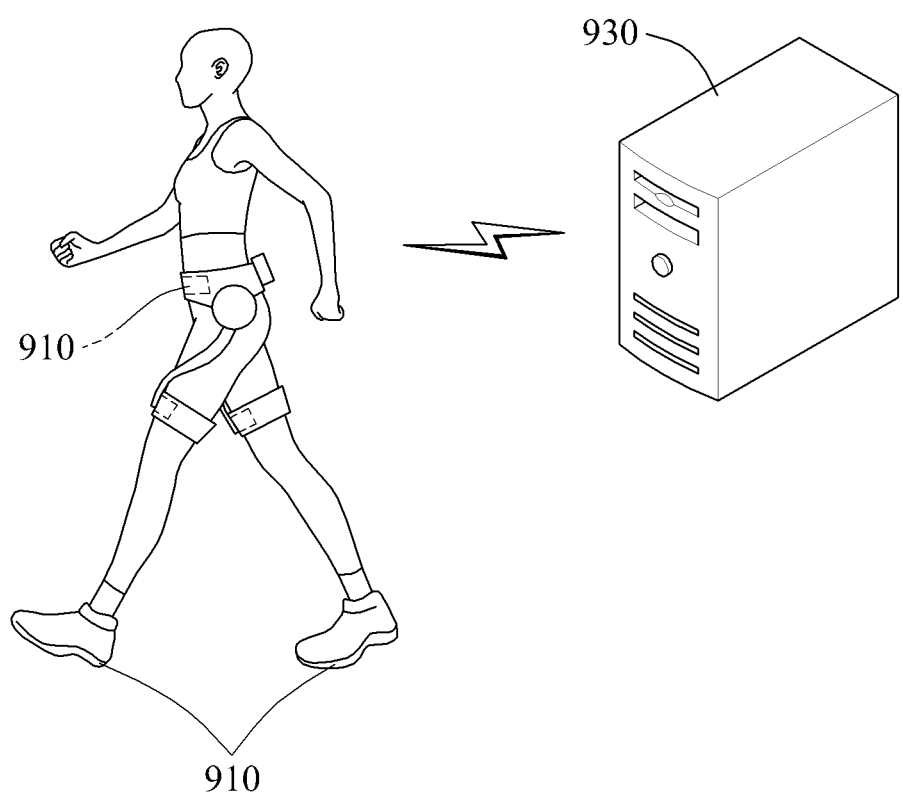
FIG. 9 illustrates provision of a feedback according to example embodiments.
Figure 10:
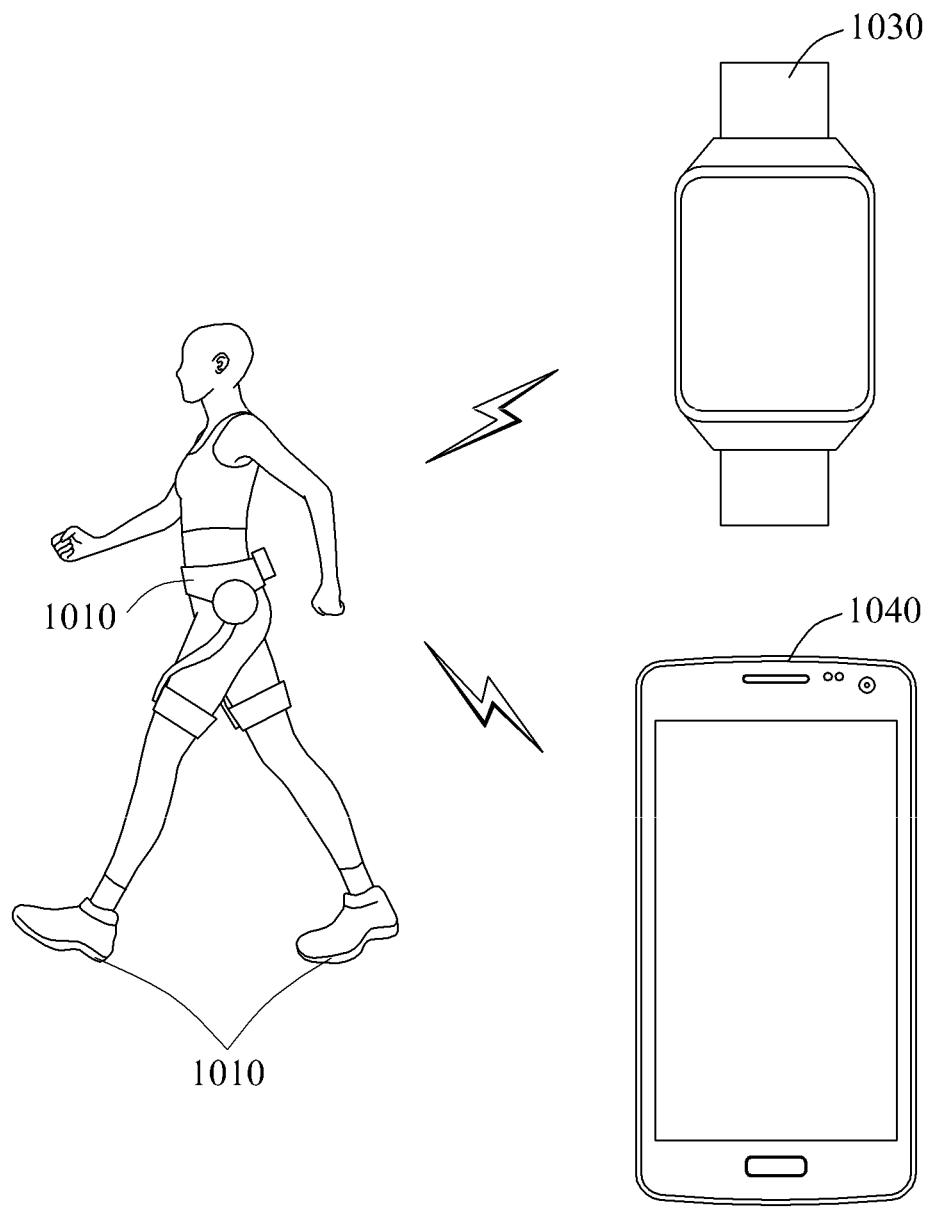
FIG. 10 illustrates an interface for provision of a feedback according to example embodiments.
Figure 11:
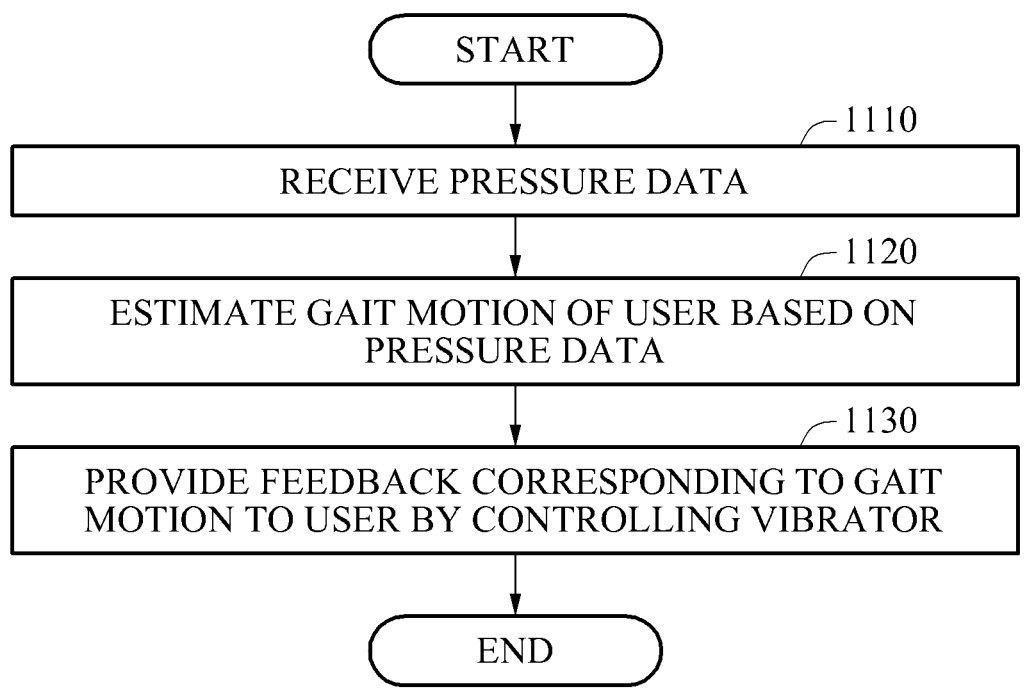
FIG. 11 illustrates a control method according to example embodiments.

The descriptions provided with reference to FIGS. 1A through 10 may be applicable to the control method of FIG. 11 and thus, duplicated descriptions will be omitted for conciseness.

Figure 2A:
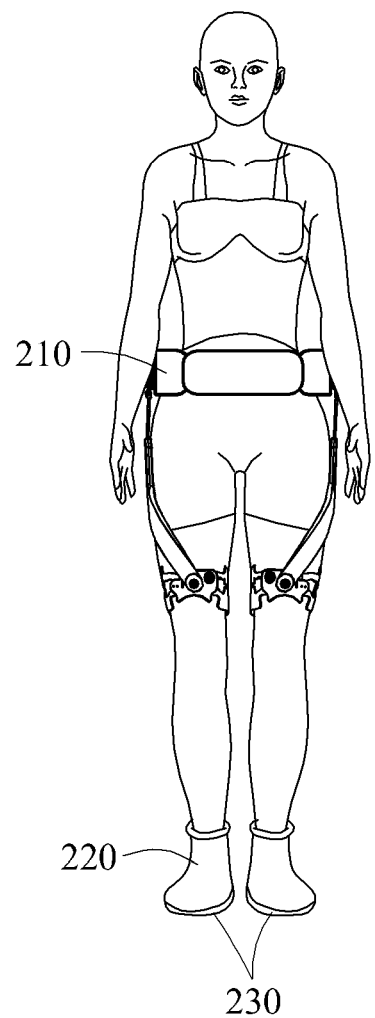
FIGS. 2A and 2B illustrate a walking assistance apparatus and an additional device according to example embodiments.
Figure 2B:
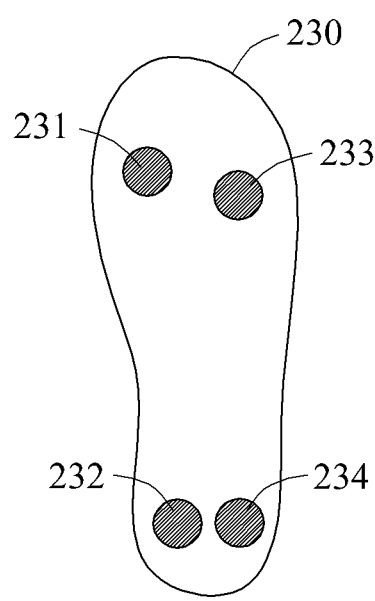

FIGS. 2A and 2B illustrate a walking assistance apparatus and an additional device according to example embodiments.

Referring to FIGS. 2A and 2B, an additional device 230 may be included in an insole of a shoe 220. The additional device 230 may include pressure sensors 231 and 232, and vibrators 233 and 234. The pressure sensors 231 and 232 may generate pressure data by sensing a pressure applied to a front and rear portions of the sole of the user while the user is walking. Further, a walking assistance apparatus 210 may generate hip joint angle data by sensing hip joint angles of the user while the user is walking.

The walking assistance apparatus 210 may interoperate with the additional device 230 through a communication interface. For example, the walking assistance apparatus 210 may receive the pressure data from the additional device 230 through the communication interface. In some example embodiments, the communication interface may include wireless Internet interfaces such as a wireless local area network (WLAN), a wireless fidelity (Wi-Fi) direct, a digital living network alliance (DLNA), a wireless broadband (Wi-Bro), a world interoperability for microwave access (Wi-MAX), and a high speed downlink packet access (HSDPA), for example, and short-range communication interfaces such as Bluetooth, a radio frequency identification (RFID), an infrared data association (IrDA), a ultra wideband (UWB), ZigBee, and a near field communication (NFC). However, example embodiments are not limited thereto. For example, the communication interface may also include all interfaces that may communicate with an external device, for example, wired interfaces.

In an example, the additional device 230 may be included in the walking assistance apparatus 210, and the additional device 230 and the walking assistance apparatus 210 may be represented as a single device.

In another example, the additional device 230 may be implemented to be in close contact with a shoe or a foot. When the walking assistance apparatus 210 supports down to an ankle or a foot or supports the entire body, the additional device 230 may be physically connected to the walking assistance apparatus 210. In this example, the additional device 230 may be considered as a part of the walking assistance apparatus 210.

The walking assistance apparatus 210 may estimate a gait motion of the user based on the pressure data received from the additional device 230. The walking assistance apparatus 210 may provide a feedback corresponding to the gait motion to the user by controlling the vibrators 233 and 234 of the additional device 230. The walking assistance apparatus 210 may provide the feedback to the user, thereby enabling the user to feel a sensation that an ordinary person would feel with a sole while walking. Accordingly, the feedback provided by the walking assistance apparatus 210 may prevent falling of the user, and may be effective in treating a user experiencing a lack of sensation in the sole.

Figure 3:
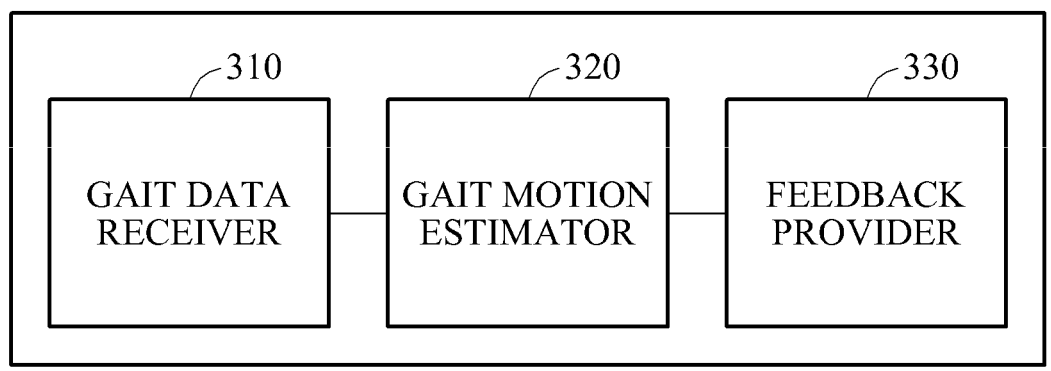
FIG. 3 illustrates a control device according to example embodiments.

FIG. 3 illustrates a control device according to example embodiments.

Referring to FIG. 3, a control device 300 may be a separate device which is physically independent from a walking assistance apparatus, or may be implemented as a logical model in a walking assistance apparatus.

For example, the control device 300 may be embodied in the controller 140, for example in the processor of the controller 140. However, example embodiments are not limited thereto.

Hereinafter, a basic unit of a gait motion may be a step or a stride. The step may include a single heel strike, and the heel strike may indicate a state in which a sole of a user touches the ground. The stride may include two steps.

The control device 300 may include a gait data receiver 310, a gait motion estimator 320, and a feedback provider 330.

The gait data receiver 310 may receive pressure data indicating information on a pressure applied to a sole of a user.

The gait data receiver 310 may receive the pressure data from a pressure sensor using a communication interface. For example, the gait data receiver 310 may receive the pressure data from a pressure sensor attached to a surface in contact with the sole of the user, for example, an insole of a shoe. At least two pressure sensors may be provided. As shown in FIG. 2B, the pressure sensors (231, 232) may be attached to a front portion and a rear portion of the insole to sense a pressure applied to a front portion of the sole of the user and a pressure applied to a rear portion of the sole of the user.

When the pressure sensor is a one-axis pressure sensor, the pressure sensor may verify whether a pressure is applied to the sole of the user. When the pressure sensor is a two or more-axis pressure sensor, the pressure sensor may sense a magnitude of a pressure applied to the sole of the user.

Further, the gait data receiver 310 may receive hip joint angle data indicating information on a hip joint angle of the user. For example, the gait data receiver 310 may receive the hip joint angle data from a sensor configured to sense a motion of a hip joint with respect to a gait motion of the user. The gait data receiver 310 may receive information on hip joint of the user from one or more potentiometers, and receive information on motion direction of hip joint from one or more IMU sensors. For example, the gait data receiver 310 may receive the information on both hip joints from the IMU sensor 130 of FIG. 1A. The hip joint angle data will be described in detail with reference to FIG. 6.

The gait data receiver 310 may receive the pressure data or the hip joint angle data from all sensors that may sense a change in a quantity of motion of a user with respect to a gait motion, rather than being limited to the pressure sensor, the IMU sensor, or the potentiometer. The gait data receiver 310 may receive the pressure data and the hip joint angle data from an external device.

The gait motion estimator 320 may estimate a gait motion of the user based on the pressure data. The gait motion estimator 320 may estimate a gait motion of touching the ground with the front portion of the sole and a gait motion of touching the ground with the rear portion of the sole based on the pressure data. Also, the gait motion estimator 320 may estimate a gait motion of swinging a leg of the user based on the pressure data and/or the hip joint angle data.

The details of the gait motion estimator 320 estimating a gait motion of touching the ground and/or swinging a leg of the user will be explained later on.

The feedback provider 330 may provide a feedback corresponding to the gait motion to the user by controlling a vibrator to apply a vibration to the sole of the user. For example, the feedback provider 330 may control a vibrator attached to a surface in contact with the sole of the user, for example, an insole of a shoe. At least two vibrators may be provided. For example, the feedback provider 330 may control the vibrators 233, 234 of FIG. 2B corresponding to the gait motion.

The feedback provider 330 may operate the vibrator based on the estimation of the gait motion of touching the ground with the front portion of the sole and the gait motion of touching the ground with the rear portion of the sole. The feedback provider 330 may correspond to a control device of FIG. 6. The details of the feedback provider 330 or the control device operating the vibrator will be provided with reference to FIG. 6.

The feedback provider 330 may adjust a vibration intensity of the vibrator. The feedback provider 330 may adjust the vibration intensity of the vibrator based on a shift in a center of pressure (COP) of the sole with respect to the gait motion. For example, the feedback provider 330 may adjust the vibration intensity of the vibrator based on the magnitude of the pressure applied to the sole. The details of the feedback provider 330 or the control device adjusting a vibration intensity of the vibrator will be described in detail with reference to FIG. 7.

The gait motion estimator 320 may model gait motions of the user as a plurality of gait states, and estimate a gait state corresponding to a current gait motion of the user, among the modeled plurality of gait states, based on the pressure data and the hip joint angle data.

The gait motion estimator 320 may estimate the gait state corresponding to the current gait motion of the user, among the modeled gait states, by applying the pressure data and the hip joint angle data to a finite state machine (FSM).

Figure 4:
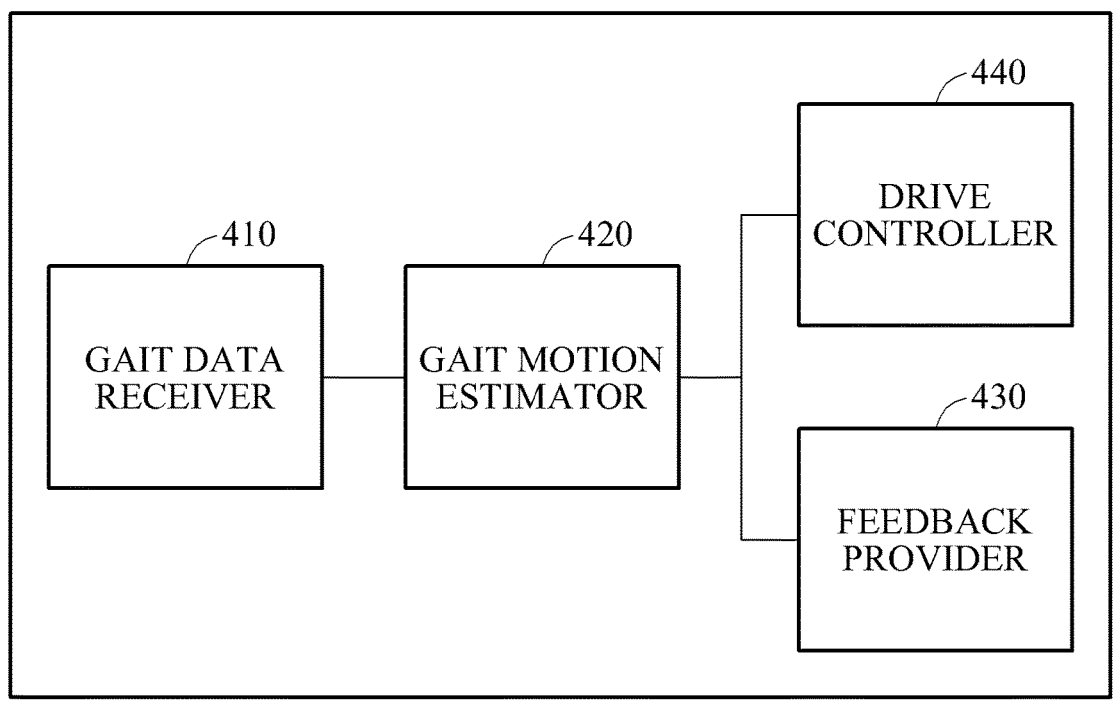
FIG. 4 illustrates a control device according to example embodiments.
Figure 6:
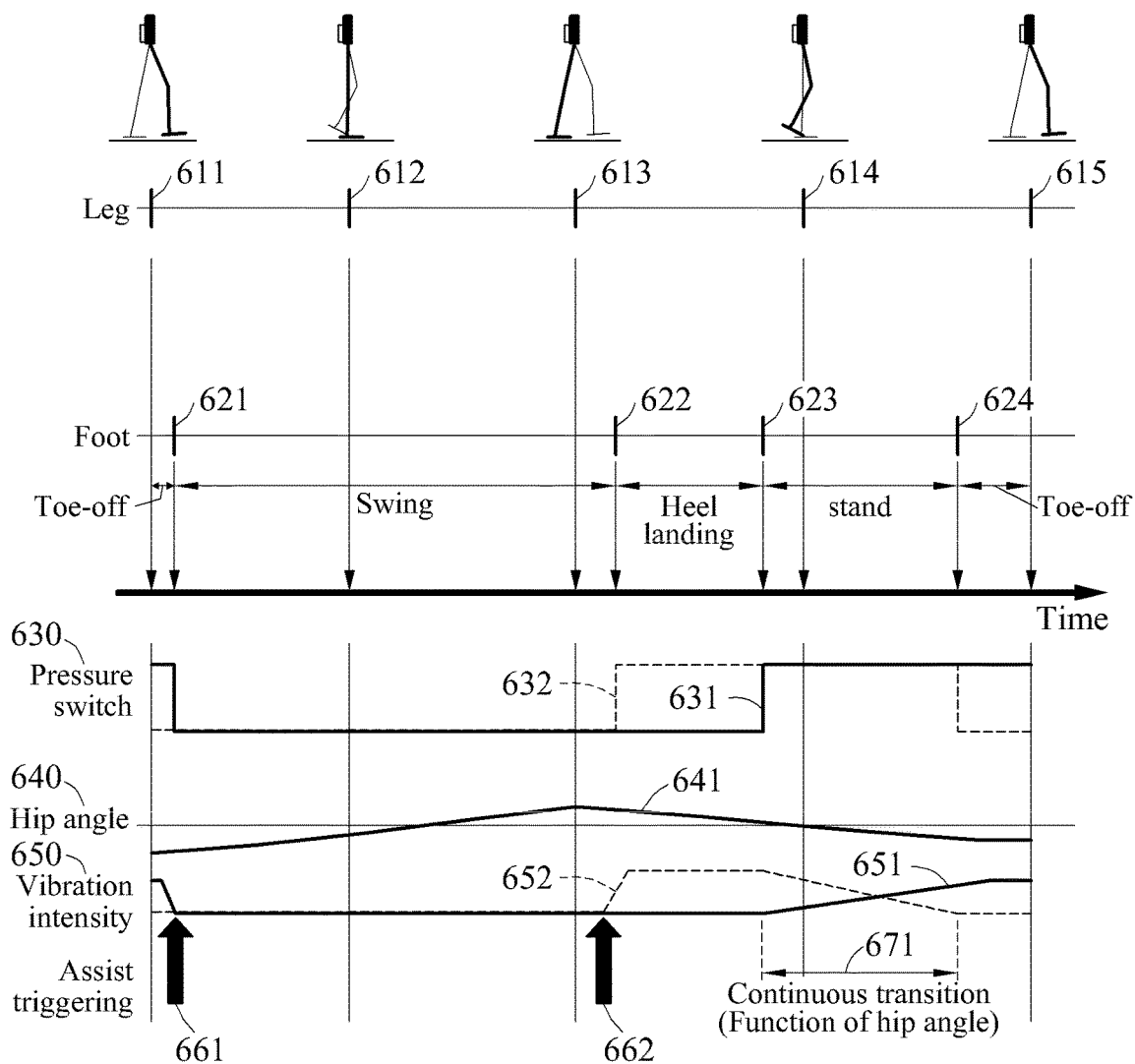
FIGS. 6 and 7 illustrate a gait motion and a feedback corresponding to the gait motion according to example embodiments.
Figure 7:
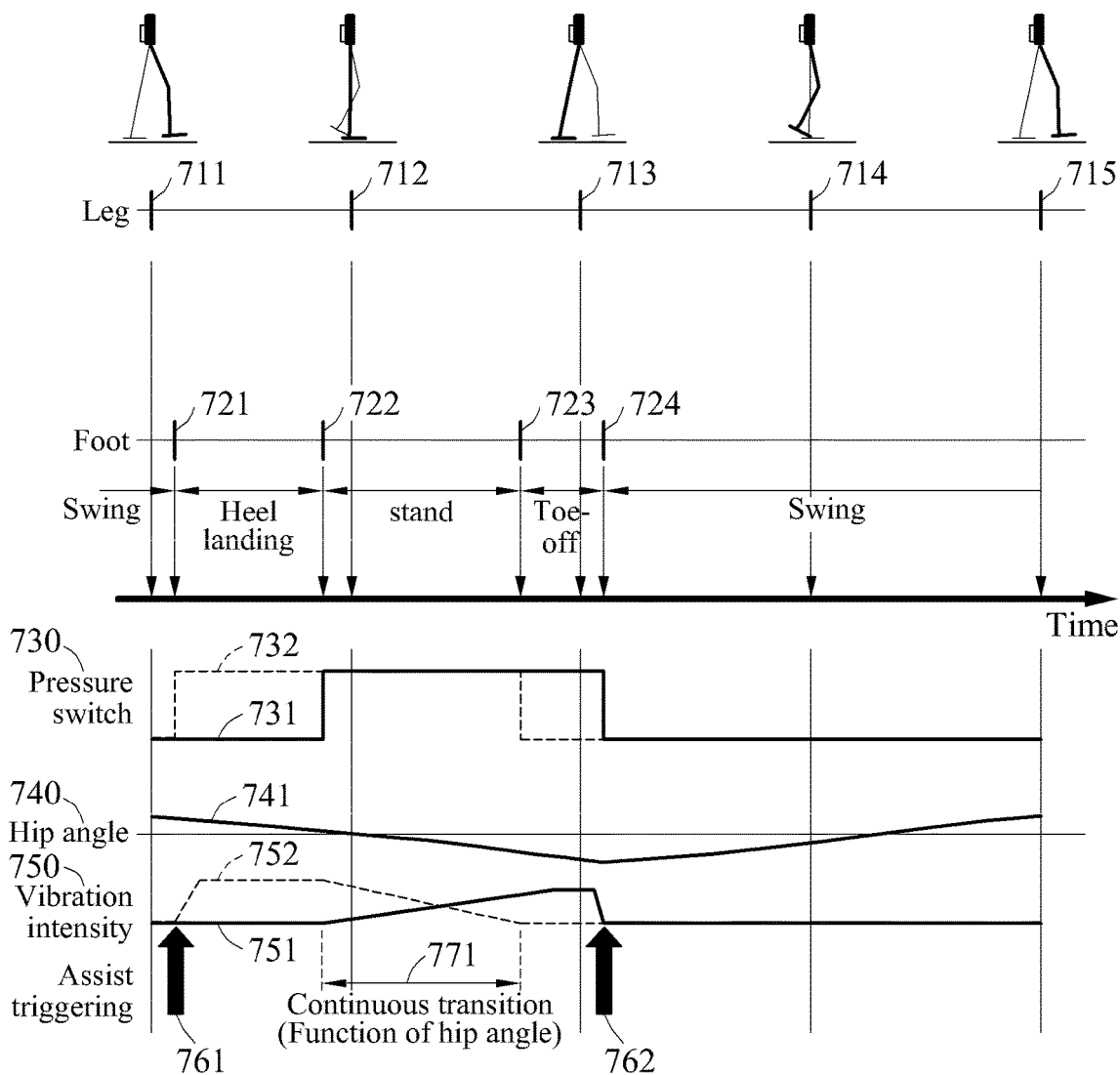

The gait motion estimator 320 may correspond to a gait motion estimator 420 of FIG. 4 or the control device of FIGS. 6 and 7. A method of estimating motions of the user using the gait motion estimator 420 or the control device will be described in detail with reference to FIGS. 4, 6, and 7.

FIG. 4 illustrates a control device according to example embodiments.

Referring to FIG. 4, a control device 400 may be a separate device which is physically independent from a walking assistance apparatus, or may be implemented as a logical model in a walking assistance apparatus.

For example, the control device 400 may be embodied in the controller 140, for example in the processor of the controller 140. However, example embodiments are not limited thereto.

The control device 400 may include a gait data receiver 410, a gait motion estimator 420, a feedback provider 430, and a drive controller 440.

The descriptions of the gait data receiver 310, the gait motion estimator 320, and the feedback provider 330 provided with reference to FIG. 3 may be applicable to the gait data receiver 410, the gait motion estimator 420, and the feedback provider 430 and thus, duplicated descriptions will be omitted for conciseness.

The drive controller 440 may control a drive of the walking assistance apparatus 100 based on the gait motion. The walking assistance apparatus 100 may include a driver configured to output an assistance force to enable both hip joints of the user to move. For example, the drive controller 440 may transmit a control signal to the driver 110 to control the driver 110 to output a gain with respect to the assistance force corresponding to the estimated gait motion. In this example, the driver 110 may output a corresponding gain based on the control signal.

The drive controller 440 may control the walking assistance apparatus based on an estimation of a gait motion of touching the ground with a front portion of the sole and a gait motion of touching the ground with a rear portion of the sole. Examples of controlling the walking assistance apparatus by the driver 440 will be described in detail with reference to FIG. 8B.

Figure 5:
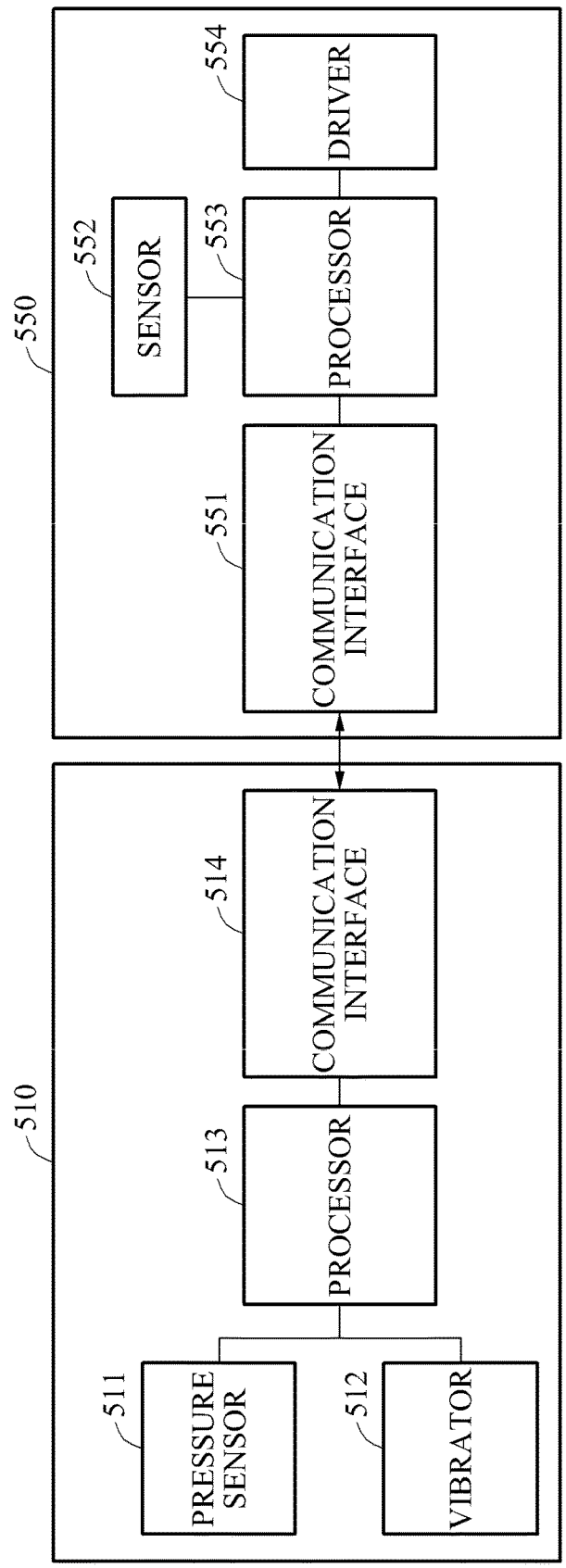
FIG. 5 illustrates a walking assistance apparatus and an additional device according to example embodiments.

FIG. 5 illustrates a walking assistance apparatus and an additional device according to example embodiments.

Referring to FIG. 5, an additional device 510 may be connected to a walking assistance apparatus 550 through their respective communication interfaces 514, 551. The additional device 510 may include a pressure sensor 511, a vibrator 512, a processor 513, and the communication interface 514.

The additional device 510 may be included in an insole of a shoe. At least two pressure sensors 511 and at least two vibrators 512 may be provided. The pressure sensors 511 may generate pressure data by sensing a pressure applied to a front portion of a sole of a user and a pressure applied to a rear portion of the sole of the user while the user is walking.

The vibrators 512 may apply vibrations to the sole of the user based on a control of the processor 513. For example, the vibrators 512 may be included in a front portion and a rear portion of the insole to apply vibrations to the front portion and the rear portion of the sole of the user.

The processor 513 may be controlled by a processor 553 of the walking assistance apparatus 550 through the communication interface 514. Based on the control of the processor 553, the processor 513 may operate the pressure sensors 511, and transmit the pressure data generated by the pressure sensors 511 to the processor 553 through the communication interface 514. Further, the processor 513 may operate the vibrators 512 and adjust a vibration intensity of the vibrators 512 based on the control of the processor 553.

The walking assistance apparatus 550 may include a communication interface 551, a sensor 552, the processor 553, and a driver 554.

In an example, the additional device 510 may be included in the walking assistance apparatus 550, and the additional device 510 and the walking assistance apparatus 550 may be represented as a single device.

The descriptions provided with respect to the potentiometer or the IMU sensor may be applicable to a sensor 522 and thus, duplicated descriptions will be omitted for conciseness.

The processor 553 may be programmed with instructions that configure the processor 553 to perform the functions of the control device 300 or the control device 400.

The descriptions provided with respect to the pressure sensors 231, 232 may be applicable to the pressure sensors 511 and thus, duplicated descriptions will be omitted hereinafter. Further, descriptions provided with respect to the driver 110 may be applicable to the driver 554 and thus, duplicated descriptions will be omitted for conciseness.

FIGS. 6 and 7 illustrate a gait motion and a feedback corresponding to the gait motion according to example embodiments.

FIG. 6 illustrates a gait motion of a left foot of a user and a feedback corresponding to the gait motion. A control device to be described with reference to FIG. 6 may be the control device 400 of FIG. 4.

In advance of describing a graph 630, a method of estimating a gait motion of the user based on the pressure data using the control device will be described.

According to an aspect, the control device may estimate a gait motion of the user based on the pressure data. The control device may estimate a gait motion of touching the ground with the front portion of the sole and a gait motion of touching the ground with the rear portion of the sole based on the pressure data. The pressure data may include information regarding whether a pressure is applied to the sole of the user.

The control device may detect a time period during which a pressure is applied to a desired (or, alternatively, a predetermined) portion of the sole from the pressure data, and estimate the detected time period to be a time period during which a gait motion of touching the ground with the desired (or, alternatively, the predetermined) portion of the sole is performed. For example, the control device may detect a time period during which a pressure is applied to the front portion of the sole from the pressure data, and estimate the detected time period to be a time period during which a gait motion of touching the ground with the front portion of the sole is performed.

The control device may detect a time period during which a pressure is applied to the rear portion of the sole from the pressure data, and estimate the detected time period to be a time period during which a gait motion of touching the ground with the rear portion of the sole is performed.

Further, when a time period during which pressures are applied to both the front portion and the rear portion of the sole is detected from the pressure data, the control device may estimate the detected time period to be a time period during which a gait motion of touching the ground with both the front portion and the rear portion of the sole is performed.

According to another aspect, the control device may estimate a gait motion of swinging a leg of the user based on at least one of the pressure data and the hip joint angle data. For example, the control device may detect a time period during which a pressure is not applied to either a front portion or a rear portion of a left sole of the user, and estimate the detected time period to be a time period during which a gait motion of swinging a left leg of the user is performed.

Further, the control device may detect a difference between angles of both hip joints from the hip joint angle data, and estimate a gait motion of swinging a leg of the user based on the difference between the angles of both hip joints.

According to still another aspect, the control device may classify the gait motion into one of a plurality of states, and model the classified gait states. For example, the control device may classify the gait motion into one of a state in which a right leg swings, a state in which both legs cross, and a state in which a left leg swings. The control device may estimate the gait state corresponding to the current gait motion of the user, among the modeled gait states, by applying the pressure data and the hip joint angle data to a FSM.

Referring to FIG. 6, the graph 630 represents pressure data with respect to time, a graph 640 represents hip joint angle data with respect to time, and a graph 650 represents operations of vibrators with respect to time. A line 631 represents pressure data obtained by sensing a pressure applied to a front portion of a left sole, a line 632 represents pressure data obtained by sensing a pressure applied to a rear portion of the left sole, a line 641 represents an angle of a left hip joint, a line 651 represents a vibration intensity of a vibrator configured to apply a vibration to the front portion of the left sole, and a line 652 represents a vibration intensity of a vibrator configured to apply a vibration to the rear portion of the left sole.

A right leg may stop swinging at a point in time 611, a left leg may swing and the left leg and the right leg may cross at a point in time 612, the left leg may stop swinging at a point in time 613, the right leg may swing and the right leg and the left leg may cross at a point in time 614, and the right leg may stop swinging at a point in time 615 as may do at the point in time 611. In detail, gait motions at the points in time 611 through 615 indicate a stride, gait motions at the points in time 611 through 613 indicate a step of the right leg, and gait motions at the points in time 613 through 615 indicate a step of the left leg.

Between a start point in time and a point in time 621, a value of the pressure data, represented by the line 631, related to the front portion of the left sole may be "1" or "on", and a control device may estimate a gait motion of touching the ground with the front portion of the left sole based on the pressure data represented by the lines 631 and 632. Accordingly, the control device may operate a vibrator from the start point in time to the point in time 621.

At the point in time 621, the value of the pressure data, represented by the line 631, related to the front portion of the left sole may be "0" or "off", and the control device may estimate a gait motion of swinging the left leg and landing the right leg on the ground based on the pressure data represented by the lines 631 and 632 and the hip joint angle data represented by the line 641. When the left leg swings, the left hip joint may rotate in a direction toward a front side of a body, for example, in a flexion direction. Accordingly, the control device may generate a control signal 661 to output an assistance force that enables the left hip joint of the user to move toward the front side of the body, and transmit the control signal 661 to a walking assistance apparatus, to assist walking of the user.

As the left leg swings and the right leg lands on the ground between the point in time 621 and a point in time 622, values of the pressure data, represented by the lines 631 and 632, related to the front portion and the rear portion of the left sole may be "0", and the value of the hip joint angle data represented by the line 641 may increase. For example, the value of the hip joint angle data represented by the line 641 may increase from −20 degrees to 20 degrees.

At the point in time 622, the value of the pressure data, represented by the line 632, related to the rear portion of the left sole may be "1", and the control device may estimate a gait motion of touching the ground with the rear portion of the left sole as the left leg stops swinging based on the pressure data represented by the lines 631 and 632. Then, as the left leg of the user lands on the ground and the right leg swings, the left hip joint may rotate in a direction toward a rear side of the body, for example, in an extension direction. Accordingly, the control device may generate a control signal 662 to output an assistance force that enables the left hip joint of the user to move toward the rear side of the body at the point in time 622, and transmit the control signal 662 to the walking assistance apparatus, to assist walking of the user.

At a point in time 623, the value of the pressure data, represented by the line 631, related to the front portion of the left sole may be "1", and the control device may estimate a gait motion of touching the ground with the front portion and the rear portion of the left sole based on the pressure data represented by the lines 631 and 632.

At a point in time 624, the value of the pressure data, represented by the line 632, related to the rear portion of the left sole may be "0", and the control device may estimate a gait motion of separating the rear portion of the left sole from the ground and touching the ground with the front portion of the left sole based on the pressure data represented by the lines 631 and 632.

Between the point in time 623 and the point in time 624, the right leg may swing and an upper body of the user may move forward by the swing of the right leg and thus, a COP of the left sole may be shifted from the rear portion to the front portion. The control device may estimate the COP based on the pressure data represented by the lines 631 and 632 and the hip joint angle data represented by the line 641. For example, the control device may detect a time period 671 between the point in time 623 and the point in time 624 during which pressures are applied to both the rear portion and the front portion of the left sole from the pressure data represented by the lines 631 and 632, and estimate that the left hip joint rotates in an extension direction in the time period 671 from the hip joint angle data represented by the line 641. A case in which the left hip joint rotates in the extension direction in the time period during which pressures are applied to both the rear portion and the front portion of the left sole may indicate that the right leg swings forward from the behind. As the right leg swings, the COP of the left sole may be shifted from the rear portion to the front portion. Accordingly, the control device may estimate the COP of the left sole to be shifted gradually from the rear portion to the front portion in the time period 671. When the COP is shifted, a magnitude of a pressure applied to the left sole may change. The control device may adjust vibration intensities of the vibrators based on the magnitude of the pressure applied to the left sole. In the time period 671, the control device may gradually decrease the vibration intensity, represented by the line 652, of the vibrator configured to apply a vibration to the rear portion of the left sole, and gradually increase the vibration intensity, represented by the line 651, of the vibrator configured to apply a vibration to the front portion of the left sole.

FIG. 7 illustrates a gait motion of a right foot of a user and a feedback corresponding to the gait motion.

Referring to FIG. 7, a graph 730 represents pressure data with respect to time, a graph 740 represents hip joint angle data with respect to time, and a graph 750 represents operations of vibrators with respect to time. A line 731 represents pressure data obtained by sensing a pressure applied to a front portion of a right sole, a line 732 represents pressure data obtained by sensing a pressure applied to a rear portion of the right sole, a line 741 represents an angle of a right hip joint, a line 751 represents a vibration intensity of a vibrator configured to apply a vibration to the front portion of the right sole, and a line 752 represents a vibration intensity of a vibrator configured to apply a vibration to the rear portion of the right sole.

A right leg may stop swinging at a point in time 711, a left leg may swing and the left leg and the right leg may cross at a point in time 712, the left leg may stop swinging at a point in time 713, the right leg may swing and the right leg and the left leg may cross at a point in time 714, and the right leg may stop swinging at a point in time 715 as may to at the point in time 711. In detail, gait motions at the points in time 711 through 715 indicate a stride, gait motions at the points in time 711 through 713 indicate a step of the right leg, and gait motions at the points in time 713 through 715 indicate a step of the left leg.

At a point in time 721, a value of the pressure data, represented by the line 732, related to the rear portion of the right sole may be "1", and a control device may estimate a gait motion of touching the ground with the rear portion of the right sole as the right leg stops swinging based on the pressure data represented by the lines 731 and 732. Then, as the right leg of the user lands on the ground and the left leg swings, the right hip joint of the user may rotate in a direction toward a rear side of a body, for example, in an extension direction. Accordingly, the control device may generate a control signal 761 to output an assistance force that enables the right hip joint of the user to move toward the rear side of the body at the point in time 721, and transmit the control signal 761 to a walking assistance apparatus, to assist walking of the user.

At a point in time 722, a value of the pressure data, represented by the line 731, related to the front portion of the right sole may be "1", and the control device may estimate a gait motion of touching the ground with the front portion and the rear portion of the right sole based on the pressure data represented by the lines 731 and 732.

At a point in time 723, the value of the pressure data, represented by the line 732, related to the rear portion of the right sole may be "0", and the control device may estimate a gait motion of separating the rear portion of the right sole from the ground and touching the ground with the front portion of the right sole based on the pressure data represented by the lines 731 and 732.

Between the point in time 722 and the point in time 723, the left leg may swing and an upper body of the user may move forward by the swing of the left leg and thus, a COP of the right sole may be shifted from the rear portion to the front portion. The control device may estimate the COP based on the pressure data represented by the lines 731 and 732 and the hip joint angle data represented by the line 741. For example, the control device may detect a time period 771 between the point in time 722 and the point in time 723 during which pressures are applied to both the rear portion and the front portion of the right sole from the pressure data represented by the lines 731 and 732, and estimate the right hip joint to rotate in an extension direction in the time period 771 from the hip joint angle data represented by the line 741. A case in which the right hip joint rotates in the extension direction in the time period during which pressures are applied to both the rear portion and the front portion of the right sole may indicate that the left leg swings forward from the behind. As the left leg swings, the COP of the right sole may be shifted from the rear portion to the front portion. Accordingly, the control device may estimate the COP of the right sole to be shifted gradually from the rear portion to the front portion in the time period 771. When the COP is shifted, a magnitude of a pressure applied to the right sole may change. The control device may adjust vibration intensities of the vibrators based on the magnitude of the pressure applied to the right sole. In the time period 771, the control device may gradually decrease the vibration intensity, represented by the line 752, of the vibrator configured to apply a vibration to the rear portion of the right sole, and gradually increase the vibration intensity, represented by the line 751, of the vibrator configured to apply a vibration to the front portion of the right sole.

In a time period between the point in time 723 and a point in time 724, the value of the pressure data, represented by the line 731, related to the front portion of the right sole may be "1", and the control device may estimate a gait motion of touching the ground with the front portion of the right sole based on the pressure data represented by the lines 731 and 732. Accordingly, the control device may operate a vibrator from the point in time 723 to the point in time 724.

At the point in time 724, the value of the pressure data, represented by the line 731, related to the front portion of the right sole may be "0", and the control device may estimate a gait motion of swinging the right leg and landing the left leg on the ground based on the pressure data represented by the lines 731 and 732 and the hip joint angle data represented by the line 741. When the right leg swings, the right hip joint may rotate in a direction toward a front side of the body, for example, in a flexion direction. Accordingly, the control device may generate a control signal 762 to output an assistance force that enables the right hip joint of the user to move toward the front side of the body, and transmit the control signal 762 to the walking assistance apparatus, to assist walking of the user.

As the right leg swings and the left leg lands on the ground between the point in time 724 and the point in time 715, the values of the pressure data, represented by the lines 731 and 732, related to the front portion and the rear portion of the right sole may be "0", and the value of the hip joint angle data represented by the line 741 may increase.

Figure 8A:
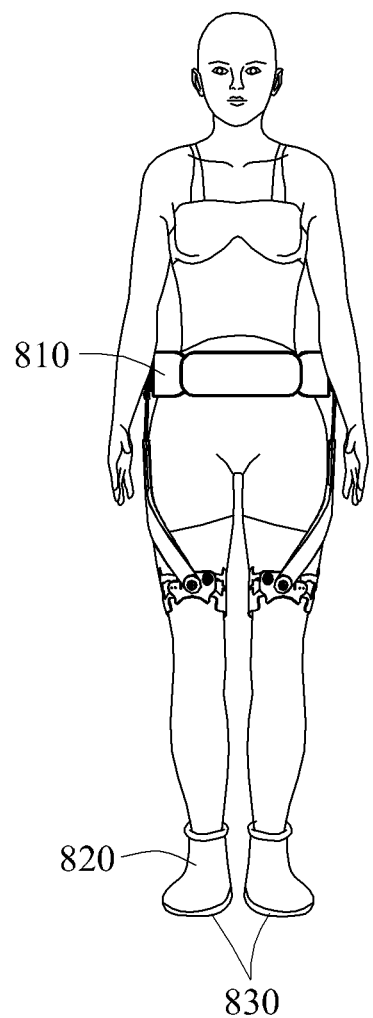
FIGS. 8A through 8C illustrate a motion assistance apparatus and additional devices according to example embodiments.
Figure 8B:
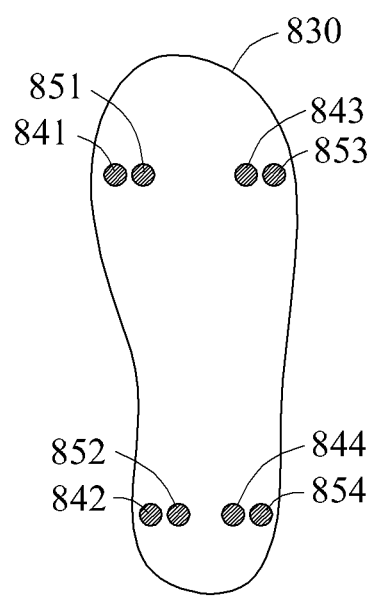
Figure 8C:
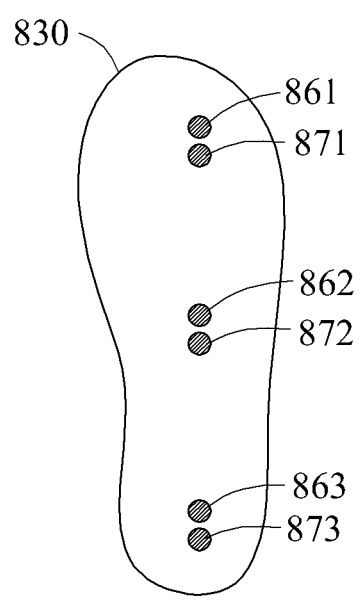

FIGS. 8A through 8C illustrate a motion assistance apparatus and additional devices according to example embodiments.

Referring to FIGS. 8A and 8B, an additional device 830 may be included in an insole of a shoe 820.

In an example, the additional device 830 may include pressure sensors 841 through 844, and vibrators 851 through 854, as shown in FIG. 8B. The pressure sensors 841 and 842 may generate pressure data by sensing pressures applied to a left portion of a sole of a user, and the pressure sensors 843 and 844 may generate pressure data by sensing pressures applied to a right portion of the sole of the user. A walking assistance apparatus 810 may receive the pressure data from the additional device 830 through a communication interface. The walking assistance apparatus 810 may determine whether a gait motion of the user is balanced based on the pressure data. For example, the walking assistance apparatus 810 may detect, from the pressure data, a time period during which pressures are applied to both the left portion and the right portion of the sole or a time period during which a pressure is not applied to either the left portion or the right portion of the sole, and determine whether a gait motion of the user is balanced in the detected time period. The walking assistance apparatus 810 may detect a time period during which a pressure is applied to the left portion or the right portion of the sole from the pressure data, and determine whether a gait motion of the user is unbalanced in the detected time period.

When the gait motion of the user is determined to be unbalanced, the walking assistance apparatus 810 may inform the user that the gait motion of the user is unbalanced by operating the vibrators 851 through 854. In this example, the walking assistance apparatus 810 may transmit a control signal to the additional device 830 or a processor configured to control the additional device 830 to operate the vibrators 851 through 854, and the additional device 830 may operate the vibrators 851 through 854 based on the control signal. For example, when the gait motion of the user leans leftward and is unbalanced, the walking assistance apparatus 810 may operate the vibrators 851 and 852. When the gait motion of the user leans rightward and is unbalanced, the walking assistance apparatus 810 may operate the vibrators 853 and 854.

Referring to FIG. 8C, in another example, the additional device 830 may include pressure sensors 861 through 863, and vibrators 871 through 873, as shown in FIG. 8C.

The pressure sensor 861 may generate pressure data by sensing a pressure applied to a front portion of a sole of a user, the pressure sensor 862 may generate pressure data by sensing a pressure applied to a central portion of the sole of the user, and the pressure sensor 863 may generate pressure data by sensing a pressure applied to a rear portion of the sole of the user. The walking assistance apparatus 810 may receive the pressure data from the additional device 830 through a communication interface. The walking assistance apparatus 810 may estimate a COP of the sole based on the pressure data. For example, when a pressure applied only to the rear portion of the sole is detected from the pressure data generated by the pressure sensor 863, the walking assistance apparatus 810 may estimate the COP to be at the rear portion of the sole. When pressures applied to the rear portion and the central portion of the sole are detected from the pressure data generated by the pressure sensors 863 and 862, the walking assistance apparatus 810 may estimate the COP to be shifted from the rear portion to the central portion of the sole. When a pressure applied only to the front portion of the sole is detected from the pressure data generated by the pressure sensor 861, the walking assistance apparatus 810 may estimate the COP to be shifted to the front portion of the sole. The walking assistance apparatus 810 may adjust vibration intensities of the vibrators 871 through 873 based on the shift in the COP.

When pressures applied to the rear portion, the central portion, and the front portion of the sole are detected from the pressure data generated by the pressure sensors 863, 862, and 861, the walking assistance apparatus 810 may calculate the COP at a portion in contact with the ground. In this example, the walking assistance apparatus 810 may control the vibrators 871 through 873 so that a vibrator closest to the COP, among the vibrators 871 through 873, may output a vibration at a greatest vibration intensity.

FIG. 9 illustrates provision of a feedback according to example embodiments.

Referring to FIG. 9, a control device may be included in a walking assistance apparatus 910 or an external device 930, for example, a server. For example, the control device 300 or the control device 400 may be included in one or more of the walking assistance apparatus 910 or the external device 930.

When the control device is included in the walking assistance apparatus 910, the control device may receive pressure data indicating information on a pressure applied to a sole of a user from a pressure sensor included in an additional device 920 through a communication interface. Further, the control device may receive hip joint angle data indicating information on a hip joint angle of the user from a sensor included in the walking assistance apparatus 910. The control device may estimate a gait motion of the user based on the pressure data, and provide a feedback corresponding to the gait motion to the user by controlling a vibrator included in the additional device 920. The control device may generate a control signal to operate the vibrator, and transmit the control signal to the additional device 920. The additional device 920 may operate the vibrator based on the control signal. The control device may estimate information on a COP of the sole based on the pressure data and the hip joint angle data, and adjust a vibration intensity of the vibrator based on a shift in the COP. The control device may control a drive of the walking assistance apparatus 910 based on the gait motion.

The control device may transmit the pressure data, the hip joint angle data, information on the gait motion of the user, information on the vibrator in operation, information on the COP, or information on the vibration intensity of the vibrator to the external device 930 through the communication interface.

When the control device is included in the external device 930, the control device may receive pressure data from the pressure sensor included in the additional device 920 through the communication interface, and receive hip joint angle data from the walking assistance apparatus 910.

The control device may estimate a gait motion of the user based on the pressure data, and provide a feedback corresponding to the gait motion to the user by controlling a vibrator to apply a vibration to a sole of the user. The control device may generate a control signal to operate the vibrator, and transmit the control signal to the additional device 920.

The control device may generate a control signal to control the walking assistance apparatus 910 to output an assistance force corresponding to the estimated gait motion, and transmit the generated control signal to the walking assistance apparatus 910. In this example, the walking assistance apparatus 910 may output an assistance force based on the control signal.

FIG. 10 illustrates an interface for provision of a feedback according to example embodiments.

Referring to FIG. 10, a control device may be included in a walking assistance apparatus 1010. For example, the control device 300 or the control device 400 may be included in one or more of the walking assistance apparatus 1010.

The control device may receive a selection of an operating mode from a wearable device 1030 or a mobile device 1040 through a communication interface. The operating mode may include a first operating mode or a normal mode in which an assistance force is provided to a user, and a second operating mode or a feedback mode in which a feedback corresponding to a gait motion is provided. When the second operating mode is selected by the wearable device 1030 or the mobile device 1040, the control device may receive pressure data indicating information on a pressure applied to a sole of the user from a pressure sensor included in an additional device 1020 through the communication interface, estimate a gait motion of the user based on the pressure data, and provide a feedback corresponding to the gait motion to the user by controlling a vibrator included in the additional device 1020. Further, the control device may receive hip joint angle data from a sensor included in the walking assistance apparatus 1010, estimate information on a COP of the sole based on the pressure data and the hip joint angle data, and adjust a vibration intensity of the vibrator based on a shift in the COP. In addition, the control device may control a drive of the walking assistance apparatus 1010 based on the gait motion.

The control device may transmit the pressure data, the hip joint angle data, information on the gait motion of the user, information on the vibrator in operation, information on the COP, or information on the vibration intensity of the vibrator to the wearable device 1030 or the mobile device 1040 through the communication interface, and the wearable device 1030 or the mobile device 1040 may display the information received from the control device.

FIG. 11 illustrates a control method according to example embodiments.

Referring to FIG. 11, in operation 1110, a control device may receive pressure data indicating information on a pressure applied to a sole of a user. For example, the gait data receiver 310 may receive pressure data from pressure sensors 231, 232.

In operation 1120, the control device may estimate a gait motion of the user based on the pressure data. For example, the gait motion estimator 320 may estimate the gait motion of the user based on the pressure data.

In operation 1130, the control device may provide a feedback corresponding to the gait motion to the user by controlling a vibrator to apply a vibration to the sole of the user. For example, the feedback provider 330 may control the vibrators 233, 234 based on the gait motion.

The descriptions provided with reference to FIGS. 1A through 10 may be applicable to the control method of FIG. 11 and thus, duplicated descriptions will be omitted for conciseness.

FIG. 12 illustrates a control method according to example embodiments.

Referring to FIG. 12, in operation 1210, a control device may receive pressure data indicating information on a pressure applied to a sole of a user. For example, the gait data receiver 410 may receive pressure data from pressure sensors 231, 232.

In operation 1220, the control device may estimate a gait motion of the user based on the pressure data. For example, the gait motion estimator 420 may estimate the gait motion of the user based on the pressure data.

In operation 1230, the control device may provide a feedback corresponding to the gait motion to the user by controlling a vibrator to apply a vibration to the sole of the user. For example, the feedback provider 430 may control the vibrators 233, 234 based on the gait motion.

In operation 1240, the control device may control a drive of a walking assistance apparatus based on the gait motion. For example, the drive controller 440 may control the driver 110 based on the gait motion.

The descriptions provided with reference to FIGS. 1A through 10 may be applicable to the control method of FIG. 12 and thus, duplicated descriptions will be omitted for conciseness.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A control device configured to control a vibrator including at least a first vibrating element and a second vibrating element associated with different portions of a sole of a user, the control device comprising:
　　a gait data receiver configured to,
　　　receive pressure data indicating information on a pressure applied to the sole of the user, and
　　　receive hip joint angle data indicating a hip joint angle of the user;
　　a gait motion estimator configured to estimate a gait motion of the user based on the pressure data; and
　　a feedback provider configured to, estimate a center of pressure (COP) of the sole based on the pressure data and the hip joint angle data, adjust an intensity of a first vibration and a second vibration based on a shift in the COP of the sole with respect to the gait motion such that, during a first step of a stride, the intensity of the first vibration continuously increases and the intensity of the second vibration continuously decreases, and control the vibrator to vibrate the sole of the user such that the first vibration is applied to the first vibrating element and the second vibration is applied to the second vibrating element.

2. The control device of claim 1, wherein the gait data receiver is configured to receive the pressure data from a pressure sensor attached to a surface in contact with the sole of the user.

3. The control device of claim 2, wherein the gait data receiver is configured to receive the pressure data from the pressure sensor via a communication interface.

4. The control device of claim 2, wherein the pressure sensor comprises:

at least two pressure sensors configured to generate the pressure data by sensing at least a front pressure applied to a front portion of the sole and a rear pressure applied to a rear portion of the sole.

5. The control device of claim 4, wherein the gait motion estimator is configured to estimate a first gait motion of touching a ground with the front portion of the sole and a second gait motion of touching the ground with the rear portion of the sole based on the pressure data.

6. The control device of claim 5, wherein the feedback provider is configured to operate the vibrator based on the first gait motion of touching the ground with the front portion of the sole and the second gait motion of touching the ground with the rear portion of the sole.

7. The control device of claim 4, wherein the feedback provider is configured to estimate the COP based on information on changes in the front pressure applied to the front portion and the rear pressure applied to the rear portion of the sole included in the pressure data.

8. The control device of claim 1, wherein
the gait motion estimator is configured to,
model the gait motion of the user into one of a plurality of gait states, and
estimate a current gait state corresponding to a current gait motion of the user, among the plurality of gait states, based on the pressure data and the hip joint angle data, and
the feedback provider is configured to control the vibrator based on the current gait state.

9. The control device of claim 5, further comprising:
a drive controller configured to control a drive of a walking assistance apparatus based on the gait motion.

10. The control device of claim 9, wherein the drive controller is configured to generate a control signal to drive the walking assistance apparatus based on the first gait motion of touching the ground with the front portion of the sole and the second gait motion of touching the ground with the rear portion of the sole.

11. The control device of claim 9, wherein
the at least two pressure sensors are configured to generate the pressure data by sensing at least a left-side pressure applied to a left portion of the sole and a right-side pressure applied to a right portion of the sole, and the gait motion estimator is configured to determine whether the gait motion of the user is balanced based on the pressure data.

12. The control device of claim 11, wherein the feedback provider is configured to operate the vibrator when the gait motion estimator determines the gait motion of the user is unbalanced.

13. The control device of claim 12, wherein the drive controller is configured to drive of the walking assistance apparatus such that the gait motion of the user is re-balanced when the gait motion estimator determines the gait motion of the user is unbalanced.

14. The control device of claim 1, further comprising:
a drive controller configured to control a drive of a walking assistance apparatus based on the gait motion.

15. A walking assistance apparatus comprising:
an interface configured to connect to a peripheral device, the peripheral device comprising a pressure sensor configured to generate pressure data indicating a pressure applied to a sole of a user;
a hip joint angle sensor configured to generate hip joint angle data indicating a hip joint angle of the user;
a vibrator including at least a first vibrating element and a second vibrating element associated with different portions of the sole of the user; and
a processor configured to,
receive the pressure data and the hip joint angle data,
estimate a gait motion of the user based on the pressure data and the hip joint angle data, and
provide a feedback corresponding to the gait motion to the user by controlling the vibrator by,
estimating a center of pressure (COP) of the sole based on the pressure data and the hip joint angle data,
adjusting an intensity of a first vibration and a second vibration based on a shift in the COP of the sole with respect to the gait motion such that, during a first step of a stride, the intensity of the first vibration continuously increases and the intensity of the second vibration continuously decreases, and
instructing the first vibrating element of the vibrator to vibrate based on the first vibration, and the second vibrating element of the vibrator to vibrate based on the second vibration.

16. The walking assistance apparatus of claim 15, wherein the pressure sensor comprises:
at least two pressure sensors configured to generate the pressure data by sensing at least a front pressure applied to a front portion of the sole and a rear pressure applied to a rear portion of the sole.

17. The walking assistance apparatus of claim 16, wherein
the at least two pressure sensors are configured to generate the pressure data by sensing at least a left-side pressure applied to a left portion of the sole and a left-side pressure applied to a right portion of the sole, and
the processor is configured to,
determine whether the gait motion of the user is balanced based on the pressure data, and
operate the vibrator when the gait motion of the user is determined to be unbalanced.

18. A control method comprising:
receiving pressure data indicating a pressure applied to a sole of a user;
receiving hip joint angle data indicating a hip joint angle of the user;

estimating a gait motion of the user based on the pressure data; and controlling a vibrator to vibrate the sole of the user by,
   estimating a center of pressure (COP) of the sole based on the pressure data and the hip joint angle data,
   adjusting an intensity of a first vibration and a second vibration based on a shift in the COP of the sole with respect to the gait motion such that, during a first step of a stride, the intensity of the first vibration continuously increases and the intensity of the second vibration continuously decreases, and
   instructing a first vibrating element of the vibrator to vibrate based on the first vibration, and a second vibrating element of the vibrator to vibrate based on the second vibration.

19. The control method of claim 18, further comprising:
driving a walking assistance apparatus based on the gait motion.

20. A non-transitory computer-readable medium comprising program code that, when executed by a processor, performs functions according to the method of claim 18.

21. A control method comprising:
generating pressure data by sensing a pressure applied to a sole of a user;
transmitting the pressure data to a walking assistance apparatus;
receiving a vibrator control signal from the walking assistance apparatus, the vibrator control signal being based on the pressure data and a center of pressure (COP) of the sole of the user, the COP determined based on the pressure data and hip joint angle data, the hip joint angle data indicating a hip joint angle of the user, the vibrator control signal including data indicating at least an intensity of a first vibration and a second vibration; and
controlling a vibrator based on the vibrator control signal by instructing a first vibrating element of the vibrator to vibrate based on the first vibration and a second vibrating element of the vibrator to vibrate based on the second vibration such that during a first step of a stride, the intensity of the first vibration continuously increases and the intensity of the second vibration continuously decreases.

22. The control method of claim 21, wherein the controlling comprises:
operating the vibrator for a time period during which a gait motion of touching a ground with the sole of the user is performed.

23. A control device comprising:
a vibrator including at least a first vibrating element and a second vibrating element associated with different portions of a sole of a user;
a pressure sensor configured to sense a pressure applied to the sole of the user;
a communication interface configured to,
   transmit pressure data to a walking assistance apparatus, and
   receive a vibrator control signal from the walking assistance apparatus, the vibrator control signal being based on the pressure data and a center of pressure (COP) of the sole of the user, the COP determined based on the pressure data and hip joint angle data, the hip joint angle data indicating a hip joint angle of the user, the vibrator control signal including data indicating at least an intensity of a first vibration and a second vibration; and
a processor configured to,
   generate the pressure data based on the sensed pressure, and
   control the vibrator based on the vibrator control signal by instructing the first vibrating element of the vibrator to vibrate based on the first vibration and the second vibrating element of the vibrator to vibrate based on the second vibration such that during a first step of a stride, the intensity of the first vibration continuously increases and the intensity of the second vibration continuously decreases.

* * * * *